United States Patent
Johnson et al.

[11] Patent Number: 6,022,343
[45] Date of Patent: Feb. 8, 2000

[54] BRIDGED COIL CATHETER SUPPORT STRUCTURE

[75] Inventors: Theodore A. Johnson, St. Paul; Paul J. Thompson, New Hope, both of Minn.

[73] Assignee: Intratherapeutics, Inc., St. Paul, Minn.

[21] Appl. No.: 09/146,933

[22] Filed: Sep. 3, 1998

[51] Int. Cl.[7] .......................... A61M 25/00; A61M 5/00; A61M 29/00
[52] U.S. Cl. .......................... 604/526; 604/523; 604/524; 604/264; 606/194
[58] Field of Search .................. 604/264, 523–28, 604/530–34; 606/194, 198; 138/138, 140–1, 141, 145–6, 153, 172

[56] References Cited

U.S. PATENT DOCUMENTS

| | | | |
|---|---|---|---|
| 4,856,516 | 8/1989 | Hillstead | 604/96 |
| 5,573,520 | 11/1996 | Schwartz et al. | |
| 5,630,829 | 5/1997 | Lauterjung | 606/198 |
| 5,693,085 | 12/1997 | Buirge et al. | 623/1 |
| 5,741,429 | 4/1998 | Donadio, III et al. | |
| 5,843,168 | 12/1998 | Dang | 623/1 |
| 5,868,782 | 2/1999 | Frantzen | 606/198 |

FOREIGN PATENT DOCUMENTS

WO 96/38193  12/1996  WIPO.

OTHER PUBLICATIONS

U.S. Patent application Ser. No. 08/985,810 entitled Catheter Support Structure, 18 pages.

*Primary Examiner*—Ronald K. Stright, Jr.
*Assistant Examiner*—Patricia M. Bianco
*Attorney, Agent, or Firm*—Merchant & Gould P.C.

[57] ABSTRACT

A catheter includes a segment having a longitudinal axis. The segment has a helical coil extending coaxially with the longitudinal axis. The coil has a plurality of turns along a length of the axis. Adjacent turns have opposing surfaces joined by bridging members tying at least selected ones of the adjacent turns.

9 Claims, 2 Drawing Sheets

6,022,343

BRIDGED COIL CATHETER SUPPORT STRUCTURE

BACKGROUND OF THE INVENTION

1. Field of the Invention

This invention pertains to catheters for passage through a vasculature system. More particularly, this invention pertains to a novel construction of at least a segment of a catheter.

2. Description of the Prior Art

Catheters are widely used in medical treatment. A catheter is an elongated flexible member advanced through a body lumen (e.g., the vasculature system) to a desired site. The catheter may be advanced over a previously inserted guide wire.

With the catheter in place, a wide variety of substances may be passed through the catheter to the site. For example, drugs may be moved through the catheter for site-specific drug delivery. Also, implements may be passed through the catheter. For example, the catheter may be used in a stent delivery system. The catheter may also be used to remove fluids from the site. Still further, a catheter may be equipped with implements (e.g., balloon tips) for performing procedures (e.g., angioplasty) at the site.

Catheters have long been used in cardiovascular treatment. More recently, catheters are used in neurological procedures requiring advancement of the catheter through very narrow vessels. To accomplish these advances, a high degree of flexibility is desired. Also, catheters need very thin walls in order to retain an internal bore having as large a diameter as possible.

Catheters are evaluated according to a variety of criteria applicable to a variety of different applications. For example, while advancing a catheter, a physician may twist a proximal end of the catheter in order to cause a corresponding twist of the distal end of the catheter (referred to as "torque transmission response"). A consistently reliable torque transmission response (e.g., a consistent one-to-one torque transmission response) is desired.

In designing catheters, it is desirable to provide a catheter which is kink resistant. Namely, a catheter typically is a tube with an internal bore of circular cross-section. When a catheter bends, it may be inclined to kink resulting in closure or geometric deformation of the circular bore. Such closure or deformation is undesirable. Further, in certain applications, the catheter may be subjected to high internal pressures (e.g., 300 psi). Such pressures tend to burst the catheter or expand the catheter geometry.

Catheter geometry can also by deformed by torque applied to the catheter. Many catheters are designed to have a reinforcing coil extending along the length of the catheter. If torque is applied in the direction of the coil winding, the internal diameter of the catheter may reduce. If torque is applied in the opposite direction, the diameter may expand. Dual coil catheters (i.e., catheters having two coils extending the length of the catheter with one coil being a clockwise wind and the other being a counter-clockwise wind) have been developed to retain dimensional stability regardless of direction of torque and to increase torque transmission. Unfortunately, such catheters are costly and have an extra layer of coil which takes up an already limited space within the vasculature.

Further, in many applications, a catheter should have a one-to-one push ratio. In other words, if a physician axially pushes a proximal end of a catheter one centimeter, it is desirable that the distal end advances a corresponding one centimeter. Similarly, a catheter should not stretch when the proximal end is axially pulled to retract the catheter or to release or deliver a device (such as a stent).

The relative importance of the afore-described attributes varies from application to application. For example, resistance to bursting may be very important where a catheter receives a drug under pressure. While still important, burst strength is not as critical in applications where the interior of the catheter is not highly pressurized.

II. SUMMARY OF THE INVENTION

According to a preferred embodiment of the present invention, a catheter is disclosed including a segment having a longitudinal axis. The segment has a helical coil extending coaxially with the longitudinal axis. The coil has a plurality of turns along a length of the axis. Adjacent turns have opposing surfaces joined by bridging members tying at least selected ones of the adjacent turns.

III. BRIEF DESCRIPTION OF THE DRAWINGS

IV. DESCRIPTION OF THE PREFERRED EMBODIMENT

Referring now to the several drawing figures in which identical elements are numbered identically throughout, a description of a preferred embodiment of the present invention will now be provided.

Figure 1:
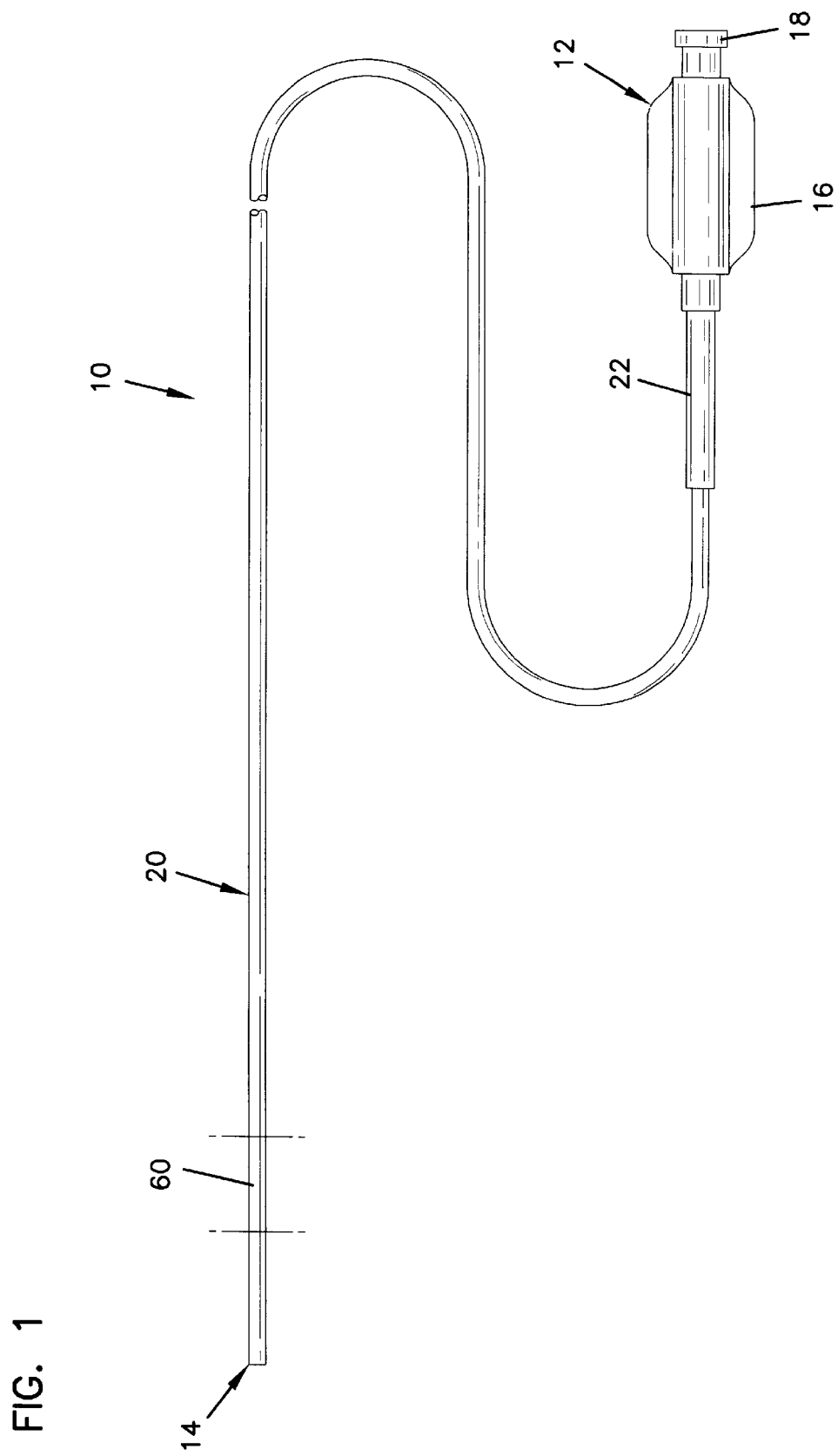
FIG. 1 is an overall view of a catheter according to the present invention.

FIG. 1 illustrates a catheter 10. The catheter 10 extends from a proximal end 12 to a distal end 14. At the proximal end 12, a hub 16 is provided to be gripped by a physician as well as having an inlet 18 for injection of fluids into the catheter 10. A flexible hollow shaft 20 is connected to the hub 16. The shaft 20 is sized to be inserted into a patient's vasculature. The shaft 20 is commonly about 100 cm long. A strain relief jacket 22 connects the shaft 20 to the hub 16. The foregoing description forms no part of this invention and is given to facilitate an understanding of the present invention.

The catheter 10 includes a segment 60 having the novel construction of the present invention. (For purposes of the remainder of this description, the word "catheter" is generally used to refer to the flexible shaft 20 of FIG. 1 having the segment 60 with a construction as will be described.) While the entire length of the catheter 10 can be constructed as will be described with reference to segment 60, it may be desirable to have a catheter 10 of multiple segments of different construction to impart different properties to different regions of the catheter 10 along its length. For example, it may be desirable to provide a catheter 10 having a proximal portion stiffer than a more flexible distal portion. While the present invention is suitable for forming catheter segments of varying degrees of flexibility and other properties, the present invention is described with reference to a segment 60 of the length of the catheter 10. This is to allow for catheters where the entire length is constructed according to the teachings of this application as well as catheters where only a discrete portion is so constructed and where the remainder is constructed according to conventional catheter construction techniques.

Figure 2:
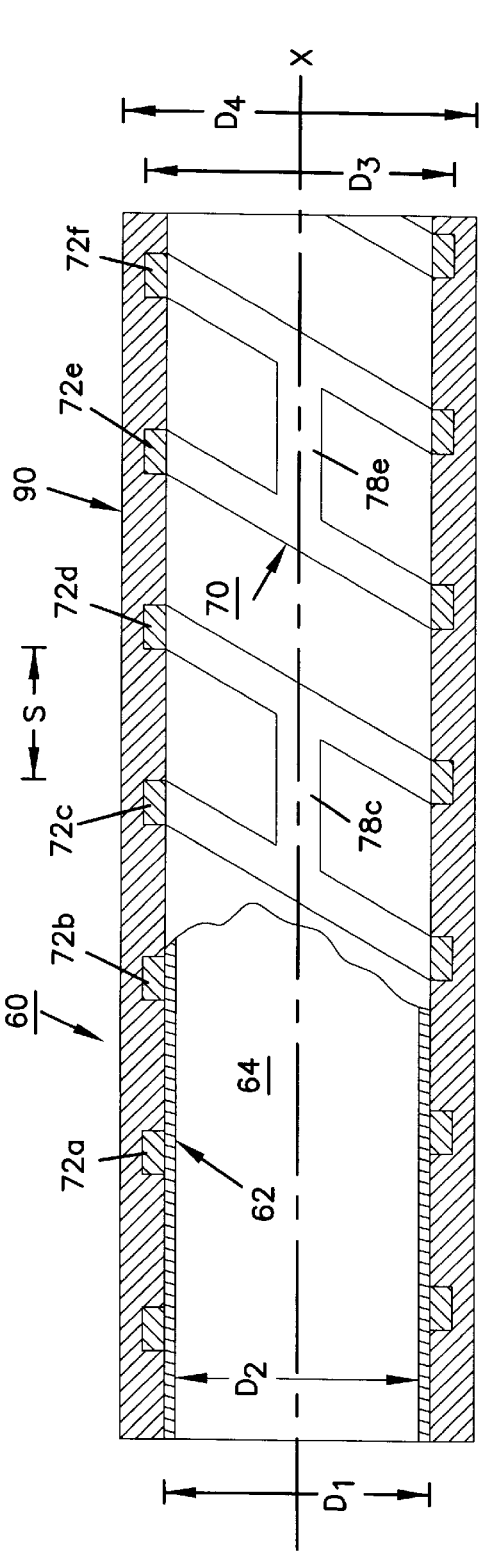
FIG. 2 is a cross-sectional, longitudinal view of a longitudinal segment of the catheter of FIG. 1.
Figure 3:
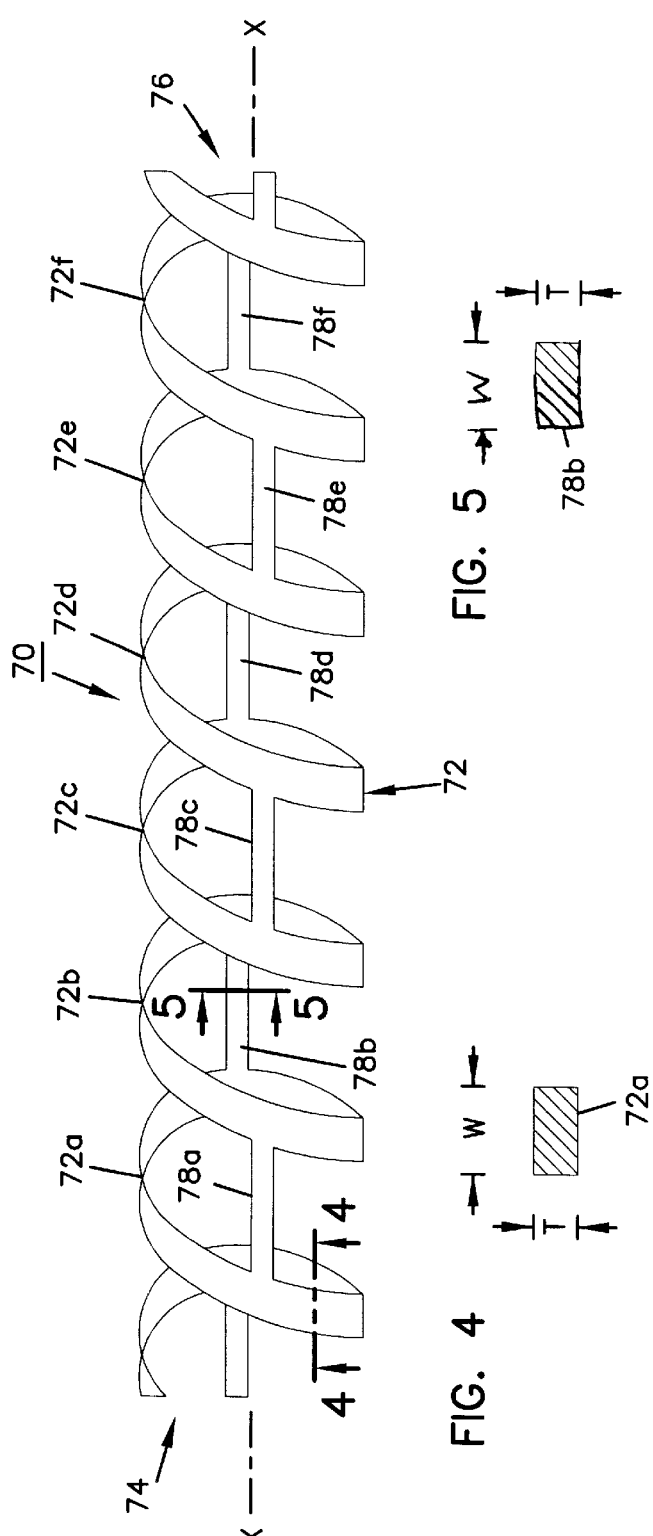
FIG. 3 is a perspective view of a support structure of the segment of FIG. 2.

With reference to FIGS. 2 and 3, the segment 60 is shown to illustrate the novel construction. The segment 60 is a multi-layer construction including a flexible tubular inner layer 62. By way of non-limiting example, the inner layer 62 is polytetraflouroethylene (PTFE) more commonly known by the trademark Teflon™. In a preferred embodiment, layer 62 has an outer diameter $D_1$ of 0.093 inch (2.36 mm) and an inner diameter $D_2$ of 0.0910 inch (2.30 mm) to define an internal bore 64 surrounded by the Teflon inner tube layer 62.

The segment 60 also includes a novel support structure 70 as will be more fully described. The support structure 70 is generally tubular and has an outer diameter $D_3$ of about 0.100 inch (2.54 mm).

Surrounding the exterior of the support structure 70, an outer polymer jacket 90 is provided. The outer jacket 90 may be any suitable flexible material for use in the vascular system. Such materials may be nylon or urethane or polyetherblock amide (PEBA). The outerjacket 90 has an outer diameter $D_4$ of 0.105 inch (2.67 mm).

In the foregoing, Applicants have provided a specific description of various layers of segment 60 as well as describing specific materials and dimensions. Such specificity has been given to describe a preferred embodiment of a specific catheter 10 utilizing the novel support structure 70 as will be described. More or fewer layers of materials could be used with structure 70 to impart desired properties (e.g., varying stiffness, strength, etc.) to segment 60. Similarly, specific materials and dimensions may be varied to alter the properties of segment 60.

Referring now to FIG. 3, the novel support structure 70 of the present invention will now be described. While having an open structure, support structure 70 is generally tubular and extends from a first end 74 to a second end 76. The support structure 70 surrounds the longitudinal axis X—X. As indicated, the length of the support structure 70 (i.e., the distance between ends 74, 76) may be the entire length of the catheter or only a portion of the entire length.

The support structure 70 includes a helical coil 72 having a helical axis being co-linear with axis X—X. The coil 72 has a plurality of windings 72a–72f between ends 74, 76. While the helix 72 is shown as a counterclockwise helix when viewed from end 74, the helix could be a clockwise helix or a combination of clockwise and counterclockwise turns as shown in commonly assigned and co-pending U.S. patent application Ser. No. 08/985,810 filed Dec. 5, 1997.

The support structure further includes a plurality of bridging members 78a–78f connecting opposing ones of the windings 72a–72f. As shown, the bridging members 78a–78f extend parallel to the axis X—X. The bridging members 78a–78f are not in linear alignment. Instead, the bridging members 78a–78f are staggered around the axis X—X. For example, bridging member 78b is 180° offset from bridging member 78a. Similarly, bridging member 78c is 180° offset from bridging member 78b but is linearly aligned with bridging member 78a.

By way of example, the helical coil 72 and the bridging members 78a–78f have a width W of about 0.014 inch (0.355 mm). In the case of the bridging members 78a–78f, the width is the dimension perpendicular to the axis X—X (i.e., along section line 5—5). In the case of the helical coil 72, the width is the dimension transverse to the helical path of the helical coil 72 (i.e., along section line 4—4). The helical coil 72 and the bridging members 78a–78f have a thickness T of about 0.015 inch (0.381 mm) (i.e., the radial dimension measured between the inner and outer diameters of the helical coil 72 and the bridging members 78a–78f). Finally, the windings 72a–72f of the helical coil 72 have an axial spacing S between opposing windings 72a–72f of about 0.010 inch (0.254 mm).

Preferably, the support structure 70 is fabricated from a solid blank of medical grade stainless steel tubing such that after such fabrication the helical coil 72 and the bridging members 78a–78f are integrally and continuously formed of uninterrupted metal. Other possible materials include nickel-titanium alloys (e.g., nitinol) and cobalt-chromium-nickel alloys (e.g., Elgiloy™ alloy of Elgiloy, Inc. of Elgin, Ill. U.S.A.). Such a fabrication process includes starting with a rod (not shown) having an outer diameter equal to the desired inner diameter of the PTFE layer 62. The PTFE layer 62 is placed over the rod. The rod acts as a jig to hold the elements of catheter 10 during fabrication. A solid tube of medical grade stainless steel (referred to as a hypotube) is then adhered to PTFE layer 62 (e.g., with adhesive). As an alternative, the PTFE layer 62 and the metal tube can be assembled without the adhesive with parts held in alignment until the final outer layer 90 is applied.

The solid metal tube is then milled to remove excess material of the tube as waste and leaving only the material of the helical coil 72 and the bridging members 78a–78f as the support structure 70. In a preferred embodiment, the metal tube is milled by a chemical milling process. In such a process, a pattern mask of the desired pattern of the helical coil 72 and the bridging members 78a–78f is placed over the metal tube. A light source sensitizes a photoresist applied to the metal to create a pattern on the metal tube matching the mask. The photo-sensitized tube is then chemically etched to dissolve away the areas of the tube corresponding to the waste leaving only the desired material of the helical coil 72 and the bridging members 78a–78f. It will be appreciated that this description of a chemical milling of the metal tube forms no part of this invention per se. Such a process is more fully described in commonly assigned and copending PCT International application Ser. No. PCT/US96/08232 published on Dec. 5, 1996 as International Publication No. WO96/38193 and commonly assigned U.S. Pat. No. 5,741,429 issued Apr. 21, 1998.

After the tube is so milled, the outer layer 90 is applied to the outer surface of the support structure 70. The material of the outer layer 90 may, at the option of a designer, fill in the axial spacing S between the windings 72a–72f or leave such spacing as voids to enhance flexibility. The rod is then removed from the PTFE layer 62 leaving a completed segment 60.

Figure 4:
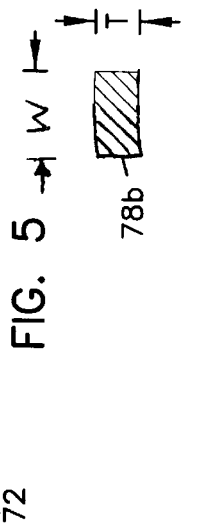
FIG. 4 is a view taken along line 4—4 in FIG. 3.
Figure 5:
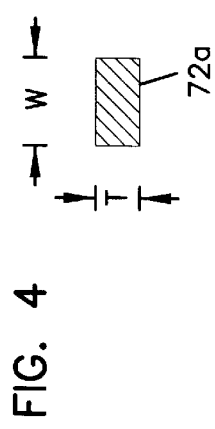
FIG. 5 is a view taken along line 5—5 in FIG. 3.

As a result of the process, the cross-section of the coil 72 is substantially rectangular (FIG. 4). The cross-section of the bridging member is also rectangular but has a more pronounced curvature to upper is and lower surfaces (FIG. 5).

Having described the structure and fabrication of the catheter segment 60 in a preferred embodiment, the benefits of the present invention will be apparent to one of ordinary skill in the art. The catheter of the present invention is highly flexible, burst resistant and has a reliable push ratio and low stretch on pull-back. All structural elements are in a common cylindrical surface thereby facilitating a thin-wall construction. Also, the structure may be easily modified (e.g., varying pitch of coil 72, spacing between windings 72a–72f, and the size and circumferential spacing of bridging members 78a–78f) to permit a catheter designer to vary properties as desired.

The coil 72 is torque responsive and burst resistant. The bridging members add kink resistance and enhance one-to-one push responsiveness and prevent stretching during pullback.

The present invention has been described in a preferred embodiment and may be modified while keeping with the teachings of the present invention. For example, the support structure 70 need not be formed of metal or fabricated in the chemical milling manner indicated. The support structure 70 can be formed from any structural material in any manner including, without limitation, electrical discharge machining, laser cutting, or assembly of individual components.

Similarly, while a preferred support structure 70 has been disclosed, numerous modifications can be made to the structure to vary the properties of the catheter 10 to meet design objectives for a specific application. For example, the spacing between windings may be varied as well as the pitch of the windings. Further, the bridging members 78*a*–78*f* need not be circumferentially spaced at 180° intervals but could be spaced differently (e.g. at 90° or 120° intervals or with some linearly aligned). Also, not all opposing windings 72*a*–72*f* need be bridged. Leaving un-bridged adjacent windings will increase flexibility. Also, bridging members 78*a*–78*f* need not be parallel to axis X—X and need not have the same thickness and width as the coil 72.

From the foregoing, the present invention has been disclosed in a preferred embodiment. The invention permits construction of a catheter overcoming disadvantages of prior designs as well as providing a structure having various features which can be modified to design catheters with optimum performance for a wide variety of applications. It is intended that modifications and equivalents of the disclosed concepts, such as those which readily occur to one of skill in the art, shall be included within the scope of the claims appended hereto.

What is claimed is:

1. An intraluminal member for insertion into a body lumen, the intraluminal member including a segment of tube having a longitudinal axis, said segment and a lumen comprising:

a wall helical coil extending coaxially with the longitudinal axis and enbedded in soil wall;

the coil having a plurality of turns along a length of the axis with adjacent turns having opposing surfaces;

bridging members tying at least selected ones of the adjacent turns.

2. An intraluminal member according to claim 1 wherein both the coil and the bridging members are contained on a common cylindrical surface.

3. An intraluminal member according to claim 1 wherein the coil is substantial rectangular in cross-section.

4. An intraluminal member according to claim 1 wherein the bridging members are parallel to the longitudinal axis.

5. An intraluminal member according to claim 1 wherein the bridging members are circumferentially spaced about the longitudinal axis.

6. An intraluminal member according to claim 1 wherein the coil and bridging members are disposed surrounding the external surface of the elongated inner layer.

7. An intraluminal member according to claim 1 further comprising a flexible outer layer surrounding an outer surface of said coil and bridging members.

8. An intraluminal member according to claim 1 wherein said segment of tube is sized to fit within a blood vessel.

9. An intraluminal member according to claim 1 wherein said tube wall includes an inner layer of flexible material surrounded by said coil and bridging members and an outer layer of flexible material surrounding said coil and bridging members, said inner layer having an inner surface defining a catheter bore.

\* \* \* \* \*

UNITED STATES PATENT AND TRADEMARK OFFICE
CERTIFICATE OF CORRECTION

PATENT NO.    : 6,022,343
DATED         : February 8, 2000
INVENTOR(S)   : Johnson et al.

It is certified that error appears in the above-identified patent and that said Letters Patent is hereby corrected as shown below:

Title page,
Item [73], "Intratherapeutics" should read -- IntraTherapeutics --

Column 1,
Line 50, "by" should read -- be --

Column 6, claim 1,
Line 4, "said segment and a lumen" should read -- and a lumen; said segment --
Line 6, insert -- ; -- after "a wall"
Line 6, insert -- a -- before "helical"
Line 7, "enbedded" should read -- embedded --

Column 6, claim 6,
Line 23, insert -- said tube wall has an elongated inner layer and wherein -- after "wherein"

Signed and Sealed this

Sixteenth Day of April, 2002

Attest:

Attesting Officer

JAMES E. ROGAN
Director of the United States Patent and Trademark Office